March 12, 1957 W. KORDES Plant Pat. 1,577
ROSE PLANT
Filed May 31, 1956
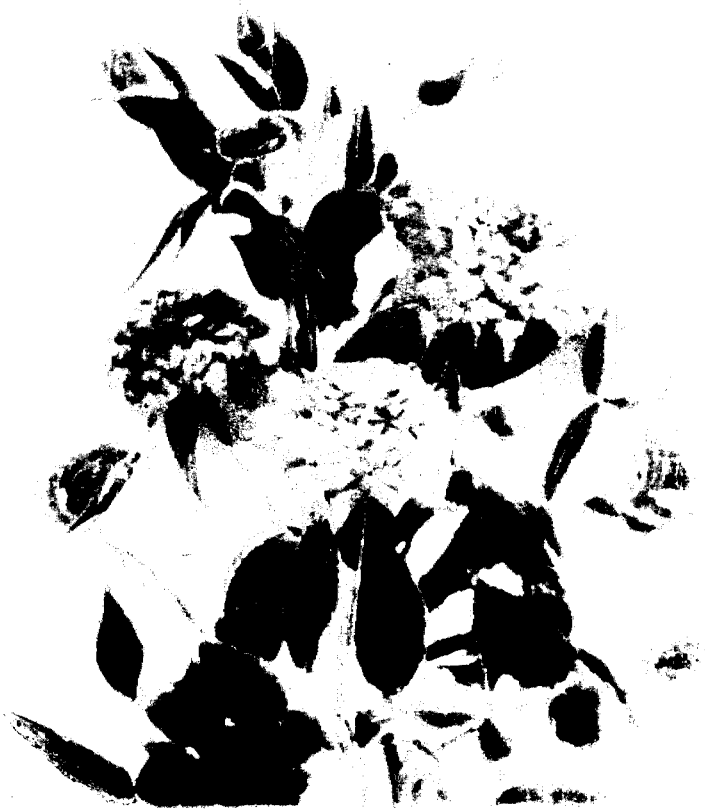
Inventor.
Wilhelm Kordes
By: Robb & Robb
Attorneys.

United States Patent Office

Plant Pat. 1,577
Patented Mar. 12, 1957

1,577

ROSE PLANT

Wilhelm Kordes, near Elmshorn in Holstein, Sparrieshoop, Germany, assignor to Jackson & Perkins Company, Newark, N. Y., a corporation of New York Application May 31, 1956, Serial No. 588,595

1 Claim. (Cl. 47—61)

The present invention relates to a new and distinct variety of rose plant of the miniature class, which was originated by me by crossing the variety known in the United States as "World's Fair," and known in Europe as "Minna Kordes" (United States Plant Patent No. 362) with the variety known in the United States as "Tom Thumb" and known in Europe as "Peon" (United States Plant Patent No. 169).

The primary objective of this breeding was to produce a new rose variety which is free-growing and freely bears dark red flowers of miniature size, while maintaining a miniature habit of growth of the plant. This objective was fully achieved, as evidenced by the fact that the new variety has inherited the color of the flowers of the parent variety "World's Fair," while at the same time has inherited the miniature flower and plant size which is characteristic of the parent variety "Tom Thumb" which is a hybrid Chinensis minima, and in addition, the new variety is importantly characterized by its free-flowering and free-growing habits. These characteristics represent a new and distinct combination of features which differentiate my new variety from its parents, as well as from all other varieties of which I am aware.

Asexual reproduction of my new variety by budding at Newark, New York, U. S. A., and also at Pleasanton, California, U. S. A., shows that the foregoing characteristics and distinctions come true to form and are established and transmitted through succeeding propagations.

The accompanying drawing shows typical specimens of the vegetative growth and flowers of my new variety in different stages of development, and as depicted in color.

The following is a detailed description of my new variety, with color terminology in accordance with Ridgway's Color Standards and Nomenclature:

Parentage: Seedling.
*Seed parent.*—"World's Fair."
*Pollen parent.*—"Tom Thumb."

Classification:
*Botanic.*—Hybrid Chinensis minima.
*Commercial.*—Miniature.

*Flower*

(Observations made from specimens grown in a greenhouse at Newark, New York, U. S. A., in the latter part of October, and about mid-morning.)

Blooming habit: Recurrent—intermittent.

Bud:
*Size.*—Small.
*Form.*—Short, with flat top; is not affected by wet or hot weather.
*Color.*—When sepals first divide—Oxblood Red, Plate 1. When petals begin to unfurl—Carmine, Plate 1, lightly overcast with Pomegranate Purple, Plate 12. When half-blown: inside of petals—Oxblood Red, Plate 1, lightly overcast with Carmine, Plate 1; reverse of petals—Pomegranate Purple, Plate 12, lightly overcast with Spinel Red, Plate 26.

*Sepals.*—Slightly branched; curl back when petals begin to unfurl. Color: inside—Pale, dull Green-Yellow, Plate 17; outside—Cress Green, Plate 31.
*Calyx.*—Color—Cress Green, Plate 31. Shape—Pear. Size—small. Aspect—smooth. Odor when rubbed—none.
*Peduncle.* — Length — short. Aspect — smooth. Strength—erect; slender. Color—Light Cress Green, Plate 31.
*Opening.*—Opens up well; is not affected by adverse weather conditions.

Bloom:
*Size.*—Small. Average size when fully expanded—¾ inch.
*Borne.*—Both singly and in irregular clusters.
*Stems.*—Short; strong.
*Form (when first opened).*—Cupped. Permanence—flattens.
*Petalage.*—Very double (many petals and stamens hidden). Number of petals under normal conditions—from 35 to 40.
*Color.*—Center of flower—Carmine, Plate 1, lightly overcast with Pomegranate Purple, Plate 12. Outer petals—Carmine, Plate 1, lightly overcast with Spectrum Red, Plate 1. Base of petals (aiglet)—Pale, dull Green-Yellow, Plate 17. Inside of petals—Carmine, Plate 1, overcast with Pomegranate Purple, Plate 12. Reverse of petals—Pomegranate Purple, Plate 12, lightly overcast with Rose Red, Plate 12. General tonality from a distance—Carmine, Plate 1, lightly overcast with Pomegranate Purple, Plate 12.
*Discoloration.*—General tonality at end of first day—Carmine, Plate 1. Second day—Carmine, Plate 1, ovrecast lightly with Pomegranate Purple, Plate 12. Third day—Carmine, Plate 1, overcast with Pomegranate Purple, Plate 12.

Petals:
*Texture.*—Leathery; is not affected by wet or hot weather.
*Appearance.*—Inside—velvety. Outside—satiny.
*Form.*—Slightly pointed.
*Arrangement.* — Imbricated (regularly arranged shingle-like).
*Petaloids in center.*—Many; small.
*Persistence.*—Drop off cleanly.
*Fragrance.*—Slight. Nature—light tea.
*Lasting quality.*—On the plant—long. As cut flower—long.

*Genital Organs*

Stamens, anthers: Small; few; mixed with petaloids. Color—Amber Yellow, Plate 16.
Stamens, filaments (threads): Short. Color—Chartreuse Yellow, Plate 31.
Pollen: Color—Massicot Yellow, Plate 16.
Styles: Bunched; uneven length; short; thin.
Stigmas: Color—Sea-Foam Green, Plate 31.
Ovaries: All enclosed in calyx.
Hips: None.
Seeds: None.

*Plant*

Form: Bush.
Growth: Medium; compact; about 15 inches in height.
Foliage: Compound of 5 to 7 leaflets.
*Size.*—Small.
*Quantity.*—Abundant.
*Color.*—New foliage: upper side—Oil Green, Plate 5; under side—Rainette Green, Plate 31. Old foliage: upper side—Forest Green, Plate 17; under side—Light Elm Green, Plate 17.
*Shape.*—Oval pointed.

*Texture.*—Upper side—glossy. Under side—smooth.
*Ribs and veins.*—Ordinary.
*Edge.*—Serrated (saw-toothed).
*Serration.*—Single; small.
*Leaf stem.*—Color—Grass Green, Plate 6. Under side—prickly.
*Stipules.*—Short; smooth.

Wood:

*New wood.*—Color—Biscay Green, Plate 17. Bark—smooth.
*Old wood.*—Color—Forest Green, Plate 17. Bark—smooth.

Thorns:

*Thorns.*—Quantity: on main stalks from base—few; on laterals from stalk—few. Form—short; straight; with narrow base. Color (when young)—Carmine, Plate 1. Position—irregular.

*Prickles.*—Quantity: on main stalks—none; on laterals—none.
*Short needles.*—Quantity: on main stalks—none; on laterals—none.

I claim:

A new and distinct variety of rose plant of the miniature class, substantially as herein shown and described, characterized particularly as to novelty by its free-growing but compact and free-flowering habits, its dark red flowers, and the good lasting qualities of its flowers as cut flowers.

No references cited.